United States Patent [19]

Task

[11] Patent Number: 4,946,282
[45] Date of Patent: Aug. 7, 1990

[54] TRANSPARENCY TRANSMISSIVITY MEASUREMENT DEVICE

[75] Inventor: Harry L. Task, Dayton, Ohio

[73] Assignee: The United States of America as represented by the Secretary of the Air Force, Washington, D.C.

[21] Appl. No.: 273,309

[22] Filed: Nov. 18, 1988

[51] Int. Cl.$^5$ .................. G01N 21/59; G01N 21/84
[52] U.S. Cl. .................................. 356/432; 356/443
[58] Field of Search ............ 356/432, 434, 443, 236; 250/228, 571

[56] References Cited

U.S. PATENT DOCUMENTS

| | | | |
|---|---|---|---|
| 1,016,753 | 2/1912 | Leumann | 250/228 |
| 1,967,583 | 7/1934 | McFarlane et al. | 356/434 |
| 3,711,701 | 1/1973 | Squyres | 356/236 |
| 3,999,863 | 12/1976 | Schoneman | 356/432 |
| 4,003,662 | 1/1977 | Retzer et al. | 356/435 |
| 4,071,299 | 1/1978 | Amano et al. | 356/443 |
| 4,094,609 | 6/1978 | Fujii et al. | 356/435 |
| 4,188,533 | 2/1980 | Ashenfelter et al. | 250/341 X |
| 4,623,258 | 11/1986 | Task et al. | 356/432 |

Primary Examiner—Vincent P. McGraw
Attorney, Agent, or Firm—Bobby D. Scearce; Donald J. Singer

[57] ABSTRACT

A device for measuring optical transmissivity of a transparency is described which comprises a diffuse light source (Lambertian diffuser) of controllable substantially constant luminance and preselected light emitting surface area for placement near a first side of a transparency for transmitting diffuse light along an optical axis through the transparency, a housing having a wall defining an aperture for placement near the second side of the transparency opposite the diffuse light source, and a detector in the form of a photo diode, cadmium sulfide cell or the like disposed within the housing and coaxial with and spaced a preselected distance from the aperture, the aperture being selected in size to expose all of the effective light detection surface area of said detector to the light emitting surface area of the diffuse light source.

21 Claims, 2 Drawing Sheets

TRANSPARENCY TRANSMISSIVITY MEASUREMENT DEVICE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for measuring transmissivity of transparencies, and more particularly to a novel field usable device for making accurate measurements of transmissivity.

Previous methods for measuring optical transmissivity of a transparency generally comprise placing a source and detector on opposite sides of the transparency to measure transmitted light. The method described in ASTM D1003-61 measures luminous transmittance through the transparency using an integrating sphere, and requires accurate alignment of source and detector. A second method utilizes a diffuse area light source of uniform luminance which is measured first directly and then through the transparency using a photometer, the transmissivity being calculated as a ratio of the luminance measured with the transparency in the path to the luminance of the source without the transparency. A difficulty with this procedure is that unwanted reflections from the transparency may cause erroneous readings. Each method requires relatively expensive equipment and a trained operator to obtain accurate results.

The invention described herein meets the need for a simple, accurate, inexpensive, field useable device to measure transmissivity of transparencies in aircraft windscreens, automotive windshields and the like. The invention includes a diffuse light source of controllable luminance for placement against one side of the transparency to be measured, and a detector for placement against the other side of the transparency, the detector including a photo diode, cadmium sulfide cell or similar detector element spaced a preselected distance from the aperture to detect only light from a preselected solid cone angle originating from a point near the detector. Although a lens may be included in the aperture of the detector in order to better collect transmitted light to the detector element, the absence of any lens in a preferred form of the invention significantly simplifies structure and use of the invention. The combination of a relatively large uniform light source and a relatively small recessed light detector element provides a condition similar to an infinite extent light source for a limited distance between light source and detector. As the distance between detector and light source increases, the area of the diffuse light source that illuminates the detector increases as the square of the distance to the detector. At the same time, the distance from any point on the surface of the light source to the surface of the detector also increases such that the illumination contribution from each light source point is decreasing with the square of the distance. These two effects exactly compensate and illumination reaching the detector remains constant throughout the distance for which these conditions pertain. This condition only occurs if the light source is a true Lambertian (substantially totally diffusing) source. For a diffuse light source of given area, any transparency with an optical thickness that falls within this constant illumination range may therefore be measured without resorting to different thickness calibration transparencies.

It is therefore a principal object of the invention to provide an improved transmissivity measuring device and method.

It is another object of the invention to provide an accurate field usable device and method for measuring transmissivity of transparencies.

These and other objects of the invention will become apparent as the detailed description of representative embodiments proceeds.

SUMMARY OF THE INVENTION

In accordance with the foregoing principles and objects of the invention, a device for measuring optical transmissivity of a transparency is described which comprises a diffuse light source (Lambertian diffuser) of controllable substantially constant luminance and preselected light emitting surface area for placement near a first side of a transparency for transmitting diffuse light along an optical axis through the transparency, a housing having a wall defining an aperture for placement near the second side of the transparency opposite the diffuse light source, and a detector in the form of a photo diode, cadmium sulfide cell or the like disposed within the housing and coaxial with and spaced a preselected distance from the aperture, the aperture being selected in size to expose all of the effective light detection surface area of said detector to the light emitting surface area of the diffuse light source.

DESCRIPTION OF THE DRAWINGS

The invention will be clearly understood from the following detailed description of representative embodiments thereof read in conjunction with the accompanying drawings wherein.

DETAILED DESCRIPTION

Figure 1:
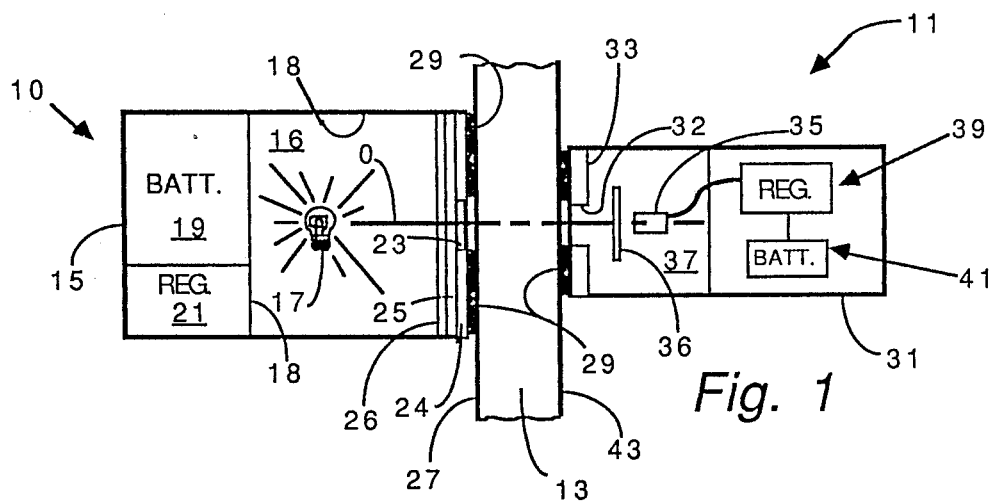
FIG. 1 is a schematic plan view of the essential components of a representative transmissivity measuring device of the invention.
Figure 2:
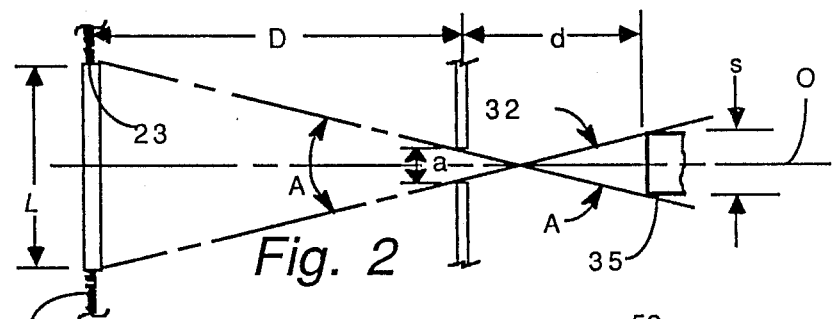
FIG. 2 is a diagram of the geometry of the optics governing operation of the FIG. 1 device.

Referring now to FIG. 1, shown therein is a schematic plan view of the essential components of an optical transmissivity measuring device of the invention. FIG. 2 illustrates the geometry of the optics governing operation of the FIG. 1 device. The invention includes two distinct components, source 10 and detector 11, which in making measurements of transmissivity are placed on respective opposite sides of and in substantial contact with transparency 13 under examination.

Source 10 comprises housing 15 containing in one compartment 16 a light source 17 and in alternate compartments power source (battery) 19 and voltage regulator and associated electronics 21. Light source 17 may comprise substantially any type as might occur to the skilled artisan. Electronics 21 include means to regulate luminance of light source 17 since it is important in the practice of the invention that a substantially constant luminance be maintained during a transmissivity measurement. Compartment 16 containing light source 17 may preferably have on the walls thereof a flat white surface 18 to provide diffuse reflection of light from light source 17. Aperture 23 or other optical opening is defined in one wall 24 of housing 15 near light source 17 substantially as shown for emitting light from housing 15 along an optical axis 0 in the operation of the invention. Aperture 23 may be any convenient preselected size (e.g. 1¼ to 2 inches) sufficient to provide a substantially uniform light emitting surface at wall 24. A Lambertian diffuser 25 is disposed at aperture 23 to ensure that the light emitting surface at aperture 23 is substantially totally diffuse. An optional filter 26 may be included in order to produce a flat spectrum of light emitted at aperture 23. Wall 24, aperture 23 and diffuser 25 are otherwise configured so that the light emitting surface defined by diffuser 25 may be placed very close to surface 27 of transparency 13. The outer surface of wall 24 defining aperture 23 may be covered with thin soft dark material 29, such as black felt, to position aperture 23 and the light emitting surface defined thereby a fixed distance from transparency 13, to act as a light shield to prevent extraneous light from entering the path between source 10 and detector 11 during a measurement utilizing the invention, and to provide a non-abrasive surface contacting transparency 13.

Detector 11 comprises housing 31 having aperture 32 (or other optical opening) in one wall 33 for admitting light projected along axis 0 from aperture 23 of source 10 through transparency 13 in performing a transmissivity measurement according to the invention. Light detector element 35 is disposed within first compartment 37 and is operatively connected to suitable support electronics 39 for processing signals from element 35 (including readout display) and power source (battery) 41 in adjacent compartment(s). Element 35 preferably comprises a photo diode or cadmium sulfide cell, photo transistor, photomultiplier tube or other photo detector element as would occur to the skilled artisan. An optional photopic filter 36 may be disposed along axis 0 as suggested in FIG. 1 for the purpose of shaping the spectral sensitivity of the system to be substantially the same as that of the human eye. Electronics 39 preferably provide both gain adjustment and zero adjustment for element 35. The outer surface of wall 33 may also be covered with material 29 surrounding aperture 32 in order to position detector element 35 a preselected fixed distance from surface 43 of transparency 13 and to block extraneous light.

FIG. 2 shows geometrical limitations on sizes of apertures 23, 32 and maximum separation D therebetween (i.e. transparency 13 thickness) for uniform illumination of detector 35. Detector 35 has an effective light detection diameter s and is disposed within compartment 37 a preselected distance d from aperture 32 so that light from a preselected cone angle A impinges onto detector 35. The diameter L of aperture 23 is therefore selected, or aperture 32 is selected to be adjustable in size, to expose to detector 35 a diffuse source of substantially uniform luminance large enough for given D to uniformly illuminate detector 35 over cone angle A defined by aperture 32 diameter a and distance d.

Figure 4:
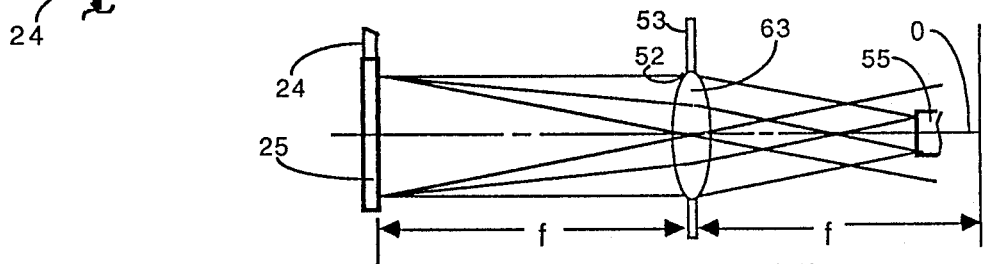
FIG. 4 is a diagram of the geometry of the optics for uniform illumination distance using an infinite source in the FIG. 3 device.
Figure 3:
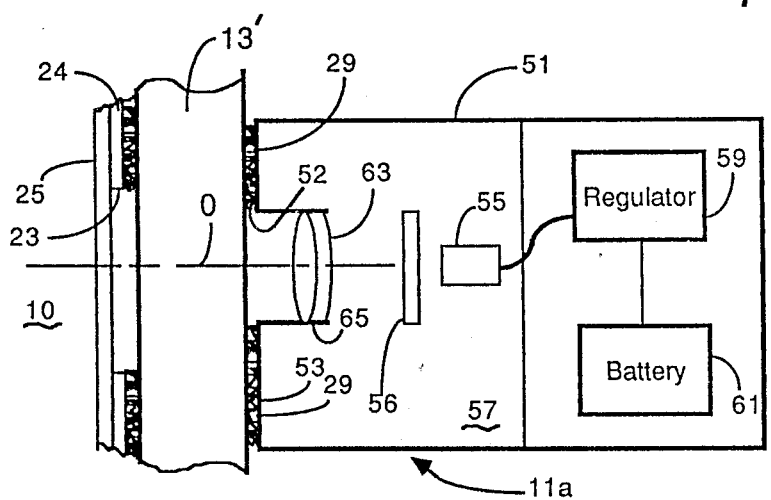
FIG. 3 is a schematic plan view of a form of the invention using a lens to achieve large uniform illumination distance.

Referring now to FIG. 3, shown therein is a schematic plan view of a form of the invention utilizing a lens inserted into the detector aperture to achieve large uniform illumination distance. FIG. 4 illustrates the geometry of the optics for uniform illumination distance using a semi-infinite source in the FIG. 3 device. As with the FIG. 1 embodiment, the FIG. 3 configuration comprises source and detector components placed on respective opposite sides of and in contact with transparency 13' under examination. The source for the FIG. 3 configuration may be the same as source 10 described above as part of the FIG. 1 device.

Detector 11a comprises housing 51 having aperture 52 in one wall 53 thereof, light detector element 55 disposed within first compartment 57 operatively connected to electronics 59 and power source 61, and photopic filter 56 each having function substantially the same as equivalently named components of the FIG. 1 device. In addition, lens 63 of focal length f (FIG. 4) is disposed at aperture 52 or, as shown in FIG. 3, disposed within mounting tube 65 and spaced a short distance from wall 53 in part to exclude extraneous light. The spacing between lens 63 and the diffuse light source at diffuser 25 in wall 24 needs to be substantially the focal length f of lens 63 in order to provide approximately maximum uniform illumination of detector 55, which considerations control the sizing of lens 63, diffuser 25 and detector 55 for measurements on transparencies 13' of given thickness, as suggested schematically in FIG. 4.

The invention as depicted in FIG. 1 is clearly the least expensive of the configurations disclosed herein, but is limited in its operation to an optical thickness range D of the transparency to be measured. However, the device of FIG. 1 has the clear advantage that it employs no lenses (63 of FIGS. 3,4) and can easily be made field portable and provides accurate, reproducible measurements by reason of the simulated infinite extent source realized by recessing detector element 35 and using a large Lambertian diffuser (25 of FIG. 1). Substantially uniform illumination of detector element 35 is achieved by providing optics with geometry suggested in FIG. 2. In the FIG. 3 embodiment, the diffuse light source appears to the detector to be magnified and, therefore, measurements of transmissivity are substantially independent of transparency thickness for a larger range of transparency optical thicknesses.

Operation of the invention may be best explained by reference to FIG. 1. The device is calibrated by placing source 10 and detector 11 against opposite sides of a calibration transparency of known transmissivity, substantially as shown in FIG. 1. Exact registration of apertures 23,33 is not required if the diffuse light source (diffuser 25) at aperture 23 is sufficiently large to subtend solid angle A defined above in relation to FIG. 2. Thickness of the calibration transparency must be within the optical thickness range D the same as that to transparencies to be tested. With source 10 turned OFF the display readout of electronics 39 of detector 11 is zeroed if required. Then with source 10 ON, detector 11 electronics 39 are adjusted to the corresponding value for the calibration transparency using the gain control. An alternate approach is to place the detector and source in direct contact with each other and set the transmissivity reading to 100 per cent. Once these adjustments are made, measurement of transmissivities of test transparencies may be made.

The transmissivity of a test (unknown) transparency 13 is measured by placing source 10 and detector 11 against the transparency as just described for a calibration transparency. Source 10 is then turned ON and the transmissivity of the transparency is read directly from the light detector system display. The test transparency need not have thickness identical to the calibration transparency if the thicknesses are in the uniform illumination region of source 10.

Figure 5:
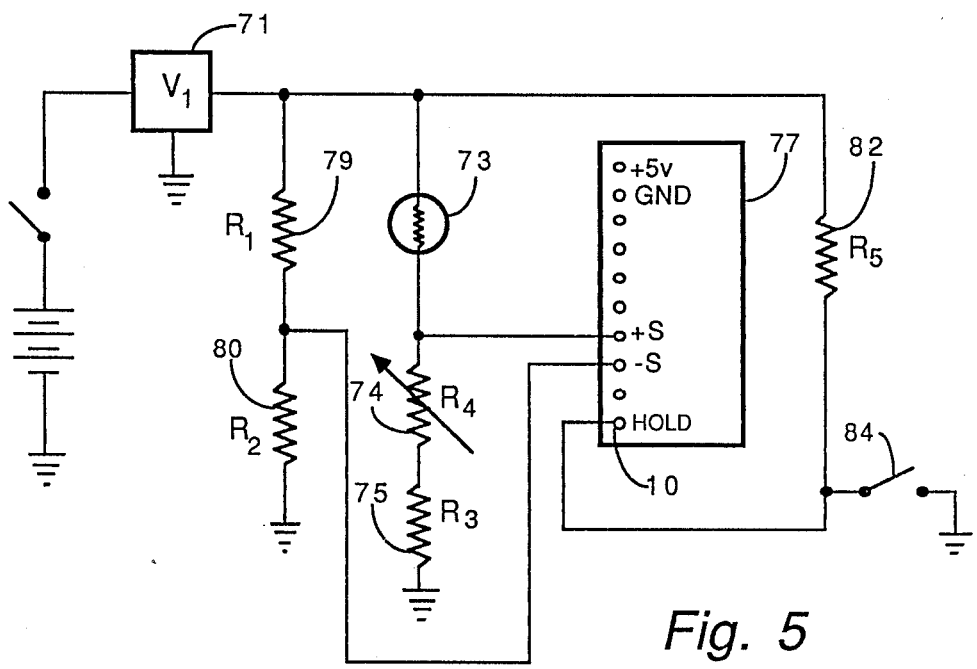
FIG. 5 is an electrical schematic of a representative circuit for controlling the detector of the FIG. 1 or FIG. 3 devices.

Referring now to FIG. 5, shown therein is an electrical schematic of a representative circuit for controlling the detector of the FIG. 1 or FIG. 3 devices. Any light sensing circuit used in the device of the invention must provide substantially linear response with light level and must have a spectral response similar to that of the human eye. Using a cadmium sulfide (CdS) cell as the light detecting element is highly desirable since resistance of a CdS cell changes with light level such that current flowing through the cell is approximately linear with the intensity of light falling on the detector, and a CdS cell has a spectral response similar to that of the human eye. The representative detector circuit of FIG. 5 includes voltage regulator 71 providing a stable voltage $V_1$ across CdS cell 73, variable resistor 74 and fixed resistor 75. Current I flowing through cell 73 and resistors 74,75 is given by:

$$I = V/(R_c + R_4 + R_3)$$

where V is the output voltage from voltage regulator 71, $R_c$ is the resistance of cell 73, and $R_4$ and $R_3$ are resistances 74,75 respectively. Resistors 74,75 are selected such that $R_c$ is substantially greater than $(R_4 + R_3)$ and current flow is primarily controlled by resistance $R_c$ which makes the circuit reasonably linear with light intensity falling on cell 73. Current I can be measured by measuring voltage S as on digital voltmeter 77 (e.g.. DP652, Acculex Co.) between cell 73 and resistor 74. Voltage S is proportional to I, viz, $$S = I(R_4 + R_3)$$

and is approximately proportional to the light level falling on cell 73. Variable resistor 74 provides calibration control to set voltage S at a level that provides meaningful readout on digital voltmeter 77, i.e., a reading of 100% with no transparency 13 between source and detector. The system therefore provides a substantially direct readout without need for calculations. Resistor 75 is a fixed off-set resistor to decrease sensitivity of the output to adjustments in resistor 74; for example, if resistor 74 is a 10-turn 2K potentiometer and resistor 75 is a fixed 2K resistor an adjustment range from 70 to 140 is obtained as $R_4$ is adjusted.

Resistors 79,80 define a voltage divider circuit which provides a low end reference for the negative input to voltmeter 77. In practice, resistor 79 is substantially larger than resistor 80 providing a very small off-set from zero,. which compensates for a non-linear nature of (CdS) cell 73 at very low light levels and for the slow response time at low light levels. Resistor 82 allows voltage to be sensed at pin 10 of voltmeter 77 which serves as a sample and hold signal. When pin 10 is at voltage V the reading is locked in the display. When pin 10 is at ground level, voltmeter 77 reads the signal level that is present between +S and −S. Switch 84 permits grounding of pin 10 for taking readings Resistor 82 serves as a buffer between ground and voltage V when switch 84 is depressed. Selecting the correct reading range of digital voltmeter 77 precludes need for amplification components, resulting in a calibrated linear light detection device with very few parts.

Figure 6:
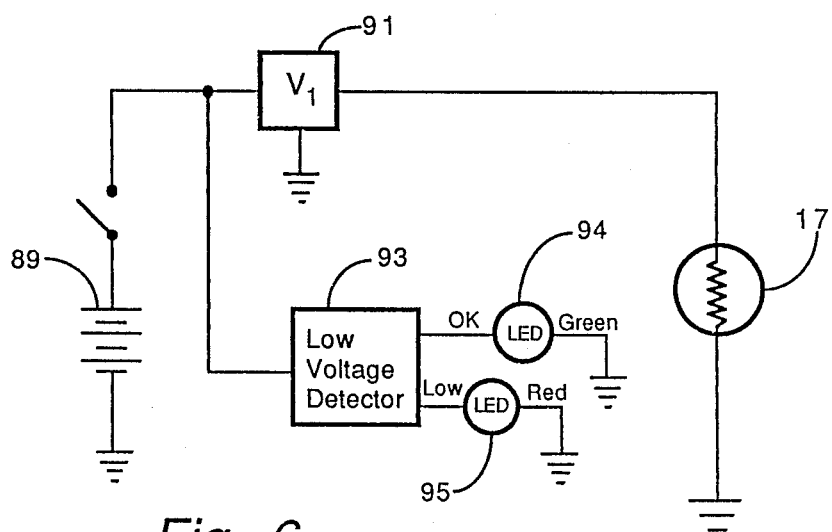
FIG. 6 is an electrical schematic of a representative circuit for controlling the source of the FIG. 1 or FIG. 3 devices.

Referring now to FIG. 6 shown therein is an electrical schematic of a representative circuit for controlling source 10 of the FIG. 1 or FIG. 3 devices. Rechargeable battery pack 89 provides power to voltage regulator 91 for providing a constant voltage to lamp 17 and for maintaining constant light output during a calibration or measurement procedure. A low voltage sensor circuit 93 is connected to the battery output to indicate proper (constant) voltage (green light emitting diode 94) or low battery voltage (red light emitting diode 95).

The invention therefore provides a field usable device for accurately measuring transmissivity of a transparency. It is understood that modifications to the forms of the invention described may be made as might occur to one skilled in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:

1. A device for measuring optical transmissivity of a transparency, comprising:
    (a) a diffuse light source of controllable substantially constant luminance and preselected light emitting surface area for placement near the surface defined by a first side of a transparency for transmission of diffuse light along an optical axis through said transparency in measuring the transmissivity thereof;
    (b) housing having a wall defining an aperture for placement near the surface defined by the second side of said transparency and substantially along said optical axis opposite said diffuse light source;
    (c) a detector having preselected effective light detection surface area disposed within said housing and coaxial with and spaced a preselected distance from said aperture; and
    (d) said aperture selected in diametric size smaller than said light emitting surface area of said diffuse light source whereby substantially all said effective light detection surface area of said detector is exposed to said light emitting surface area of said diffuse light source.

2. The device of claim 1 wherein said diffuse light source includes a substantially white incandescent source and a Lambertian diffuser.

3. The device of claim 1 wherein said detector comprises a photo diode.

4. The device of claim 1 wherein said detector comprises a cadmium sulfide cell.

5. The device of claim 1 further comprising a lens at said aperture for collecting light transmitted along said optical axis through said transparency from said diffuse light source to said detector.

6. The device of claim 1 further comprising light shielding means for excluding extraneous light from said aperture.

7. A device for measuring optical transmissivity of a transparency, comprising:

(a) a diffuse light source of controllable substantially constant luminance and preselected light emitting surface area for placement near the surface defined by a first side of a transparency for transmission of diffuse light along an optical axis through said transparency in measuring the transmissivity thereof;

(b) a housing having a wall defining an aperture for placement near the surface defined by the second side of said transparency and substantially along said optical axis opposite said diffuse light source, said aperture selected in diametric size smaller than said light emitting surface area of said diffuse light source;

(c) a detector having preselected effective light detection surface area disposed within said housing and coaxial with and spaced a preselected distance from said aperture; and (d) a lens disposed near said aperture and coaxial therewith for collecting light transmitted along said optical axis through said transparency from said diffuse light source to said detector.

8. The device of claim 7 wherein said diffuse light source includes a substantially white incandescent source and a Lambertian diffuser.

9. The device of claim 7 wherein said detector comprises a photo diode.

10. The device of claim 7 wherein said detector comprises a cadmium sulfide cell.

11. The device of claim 7 wherein said lens is positioned whereby the spacing between said diffuse light source and said lens with said transparency therebetween is substantially equal to or less than the focal length of said lens.

12. The device of claim 7 further comprising light shielding means for excluding extraneous light from said aperture.

13. A device for measuring optical transmissivity of a transparency, comprising:

(a) a substantially white incandescent light source of controllable intensity for projecting light along an optical axis through a transparency in measuring the transmissivity thereof;

(b) a Lambertian diffuser disposed along said optical axis for placement near the surface defined by a first side of said transparency for diffusing light transmitted along said optical axis through said transparency in measuring the transmissivity thereof;

(c) a housing having a wall defining an aperture for placement near the surface defined by the second side of said transparency and substantially along said optical axis opposite said diffuser, said aperture selected in diametric size smaller than the light emitting surface area of said diffuser;

(d) a detector having preselected effective light detection surface area disposed within said housing and coaxial with and spaced a preselected distance from said aperture; and (e) said aperture selected in size to expose said effective light detection surface area of said detector to light transmitted along said optical axis from said diffuser.

14. The device of claim 13 wherein said detector is a photo diode.

15. The device of claim 13 wherein said detector is a cadmium sulfide cell.

16. The device of claim 13 further comprising light shielding means for excluding extraneous light from said aperture.

17. A device for measuring optical transmissivity of a transparency, comprising:

(a) a substantially white incandescent light source of controllable intensity for projecting light along an optical axis through a transparency in measuring the transmissivity thereof;

(b) a Lambertian diffuser disposed along said optical axis for placement near the surface defined by a first side of said transparency for diffusing light transmitted along said optical axis through said transparency in measuring the transmissivity thereof;

(c) a housing having a wall defining an aperture for placement near the surface defined by the second side of said transparency and substantially along said optical axis opposite said diffuser, said aperture selected in diametric size smaller than the light emitting surface area of said diffuser;

(d) a detector having preselected effective light detection surface area disposed within said housing and coaxial with and spaced a preselected distance from said aperture; and (e) a lens disposed near said aperture and coaxial therewith for collecting light transmitted along said optical axis through said transparency from said diffuse light source to said detector.

18. The device of claim 17 wherein said detector comprises a photo diode.

19. The device of claim 17 wherein said detector comprises a cadmium sulfide cell.

20. The device of claim 17 wherein said lens is positioned whereby the spacing between said diffuse light source and said lens with said transparency therebetween is substantially equal to or less than the focal length of said lens.

21. The device of claim 17 further comprising light shielding means for excluding extraneous light from said aperture.

* * * * *

UNITED STATES PATENT AND TRADEMARK OFFICE
CERTIFICATE OF CORRECTION

PATENT NO. : 4,946,282

DATED : August 7, 1990

INVENTOR(S) : Harry L. Task

It is certified that error appears in the above-identified patent and that said Letters Patent is hereby corrected as shown below:

On the title page, item [73], the Assignee should be deleted.

Col 4, line 61, "OFF" should read ---OFF,---.

Col 5, line 40, "e.g.." should read ---e.g.,---.

Col 5, line 54, "resistor" should read ---resistor,---.

Col 5, line 60, "zero,." should read ---zero,---.

Col 5, line 68, "readings Resistor" should read ---readings. Resistor---.

Signed and Sealed this

Third Day of March, 1992

*Attest:*

*Attesting Officer*

HARRY F. MANBECK, JR.

*Commissioner of Patents and Trademarks*